United States Patent
Lezdey et al.

(10) Patent No.: US 6,207,143 B1
(45) Date of Patent: Mar. 27, 2001

(54) ANTIMICROBIAL CAT LITTER

(75) Inventors: John Lezdey; Jarett R. Lezdey, both of Indian Rocks Beach, FL (US)

(73) Assignee: Alphamed Pharmaceutical

(*) Notice: Subject to any disclaimer, the term of this patent is extended or adjusted under 35 U.S.C. 154(b) by 0 days.

(21) Appl. No.: 09/491,223

(22) Filed: Jan. 25, 2000

(51) Int. Cl.⁷ ....................................... A61L 11/00
(52) U.S. Cl. ............................................... 424/76.6
(58) Field of Search ................................... 119/171, 173; 424/76.6, 404

(56) References Cited

U.S. PATENT DOCUMENTS 5,018,482 * 5/1991 Stanislowski et al. ............. 119/173
5,576,006 * 11/1996 Smith ................................... 424/404

* cited by examiner

*Primary Examiner*—S. Mark Clardy
*Assistant Examiner*—Konata M. George
(74) *Attorney, Agent, or Firm*—John Lezdey & Assoc

(57) ABSTRACT

A cat litter composition is provided which contains on the litter particles an antimicrobial composition, which is the admixture of a diquat, a polycarboxylic acid, at least one phenol compound and a carrier, which is water or alcohol-water.

10 Claims, No Drawings

ANTIMICROBIAL CAT LITTER

FIELD OF THE INVENTION

The present invention relates to cat litter containing a novel combination of compounds. More particularly, there is provided novel complexes, which provide antimicrobial and deodorizing in a clay for use as cat litter. The compounds have a broad spectrum of activity and are especially useful in killing or deactivating odor-causing microorganisms, which are in cat litter after use by a pet.

BACKGROUND OF THE INVENTION

There is a need to provide a safe and effective means for preventing bacterial growth in a litter box that can be used on or near a cat's body without adverse effects on the cat. There is a further need to provide preparations that will inhibit and/or prevent the growth of odor causing bacteria. The problem of odors from bacteria can be especially noticed in litters that are not changed daily.

Cat litters can comprise a variety of clays that may be admixed with various naturally occurring minerals, clumping agents may be added.

Previously, hexachlorophene was widely used in many cat litter compositions to kill bacteria on contact and to prevent growth of bacteria and fungus. However, the hexachlorophene was used in direct contact with skin and was absorbable. Prolonged exposure to hexachlorophene was considered as being hazardous so that it was withdrawn from use in composition for human and pets.

There is a need to provide hypoallergenic compositions, which are used on or near pet body parts for preventing bacterial and fungal growth, which do not adversely affect the cat.

Phenols are the general standard for testing against microorganisms and parasites, however, free phenols quickly evaporate.

U.S. Pat. No. 4,332,763 to Hempel et al discloses the use of a quaternary ammonium polymer obtained by the reaction of dimethyl sulfate with a mixed polymer of vinyl pyrrolidone and dimethylamino ethylmethacrylate. However, the quaternary ammonium action of this polymer degrades in clay and loses its efficacy.

U.S. Pat. No. 3,872,128 to Byck, which is herein incorporated by reference, discloses anti-microbial ammonium polymer salts which are prepared from carboxyl-containing α-olefin polymers and quaternary ammonium salts. The polymers are used to form solid polymeric articles for hospitals and patient care.

U.S. Pat. No. 3,404,134 to Rees, which is herein incorporated by reference, discloses a process for crosslinking copolymers of alpha olefin and alpha, beta ethylenically unsaturated carboxylic acid units. The copolymers are crosslinked utilizing diamine actions. None of the diamine actions are stated as being anti-microbial. Furthermore, the polymers are used to make molded articles and sheet material.

It is understood that the term "di-quat" as used herein are biocidally active di quaternary ammonium compounds when ionically bonded maintain their biological activity.

The term "polycarboxylic acid" is intended to mean a carboxylic acid compound having 2–4 carboxylic acid groups or anhydrides which when reacted behave as polycarboxylic acids or salts thereof.

SUMMARY OF THE INVENTION

The invention provides novel cat or kitty litter compositions that contain antimicrobial complexes which are formed between poilycarboxylic acids, and a diquaternary ammonium compound and phenols. The reactions between the diquat compounds and the carboxylic acid causes at least one of the quaternary ammonium groups to coordinate or complex per molecule of polycarboxylic acid to form a more stable higher molecular weight compound. These higher molecular weight species possess the full activity of the smaller unreacted diquat but are more resistant to degradation in clays. Complexes are also formed by the phenols with the polycarboxylic acids and the diquats so as provide longer active life and slow release of the phenols.

Advantageously, the cat litter can contain about 1 to 5% by weight of the antimicrobial composition of the invention. The litter may contain other odor absorbents, such as, a basic compound, for example, an ammonium or alkali metal carbonate, bicarbonate, phosphate or perborate which are compatible with the complexes.

DESCRIPTION OF THE PREFERRED EMBODIMENT

In accordance with the present invention there is provided an antimicrobial cat litter which contains an effective amount of the combinations of diquaterary ammonium compounds and phenols.

The reaction between these compounds containing the two quaternary amine sites, the phenol and polycarboxylic acid causes at least two functional molecules of the diquat to coordinate or complex (react) per molecule of polycarboxylic acid. This forms a more stable higher molecular weight molecule. These higher molecular weight species possess the full activity of the smaller unreacted functional molecule but are more resistant to degradation in clays. Additional complexes formed with phenol and the polycarboxylic acids are more stable and longer lasting since the newly formed molecules have increased size. The formation of these simple but larger complexes or compounds has the effect of creating a slower release type of functional compound. Therefore, a larger lasting effect is achieved with these complexes without having to use the microbial or other type of biocidal agent in higher doses or frequent doses.

It is advantageous to employ other odor absorbents or neutralizers such as a perborate, phosphate, carbonate or bicarbonate. Most preferable are ammonium carbonate and ammonium bicarbonate which neutralize acidic odorants.

A suitable litter composition can be prepared by spraying about 1 to 10% by weight preferably about 2 to 5% of a solution containing the combination of the polycarboxylic acid diquat complex and phenol complexes, about 99 to 90% by weight of a solvent, preferably water, water-alkanol or alkanol. The preferred alkanols are the lower alkanols such as ethanol or isopropanol, and optionally, an odor absorbent. Preferably, at least two different phenols are utilized.

The phenols which can be utilized include phenol, ortho phenyl phenol, meta phenyl phenol, and the halogenated phenols.

Polycarboxylic acids useful in the invention include: succinic, itaconic, maleic, fumaric, citric, oxalic, and the like. The salts thereof with anions such as citrates, succinates, fumarates, maleates, malonates, etc. can be used. Maleic anhydride and other anhydrides are considered acids for the purposes of the present invention. Preferably, they contain less than 10 carbon atoms.

The reaction between these functional or useful compounds containing the diquaternary amine sites and polycarboxylic acids causes at least two functional molecules to coordinate or complex (react) per molecule of polycarboxylic acid. This forms a higher molecular weight molecule. These higher molecular weight species possess the full activity of the smaller unreacted functional molecule but are more hypoallergenic. The formation of these simple but larger complexes has the effect of creating a slower release type of functional compound and the phenol. Therefore, a larger lasting effect is achieved with these complexes without having to use the microbial or other type of biocidal agent in higher doses or frequent doses.

Antimicrobial compounds used in the invention have the general formula:

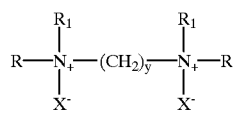

wherein:
X is halogen or hydrogen;
Y is an integer of 1 to 6;
R is hydrogen or an alkyl of 1–7 carbon atoms; and
$R_1$ is hydrogen or alkyl of 1–7 carbon atoms.

Preferred antimicrobial compounds are the quaternary alkyl pentamethyl diammoniuim compounds.

A preferred antimicrobial compound which is used in the invention is sold by Witco Corp. of Dublin, Ohio under the trademark ADOGEN (N, N, N, $N^1,N^1$-pentamethyl, $N^1$-tallow alkyl-1,3-propanamine diammonium chloride, N-tallow pentamethyl propane diammonium chloride and N-oleyl-1,3 propane diamine.

Suitable solutions of antimicrobial composition can be prepared by admixing the following:
About 0.2 to 1.0 percent by weight of a polycarboxyic acid;
About 0.2 to 1.0 percent by weight of a dignat;
About 0.8 to 2.0 percent by weight of at least one phenol compound and the remainder being water or alkanol-water.

The complex with a polycarboxylic acid and quaternary ammonium compound of the invention can be generally prepared as follows:

A solution of the polycarboxylic acid in water or water-alcohol is formed either as the ammonium or sodium salt with ammonium or sodium hydroxide, respectively. The anti-microbial compound is dissolved in water or a water-soluble solvent. The molecular ratio of anti-microbial compound to sodium or ammonium carboxylate groups in the acid or mixture of acids is adjusted to one or less than one by varying the quantity of solution to be added to the acid solution. The appropriate amounts of the two solutions are mixed with stirring. The complex forms quickly. This complex can be treated with a phenol compound added directly into the mixture.

Alternatively, the polycarboxylic acid can be directly mixed with the diquat and the phenol. The litter of the present invention can be used for other pets, for example, bird cages.

The following examples are illustrative of the invention but are not to be construed as to limiting the scope thereof in any manner. The percentages disclosed herein relate to percentages by weight unless otherwise stated.

EXAMPLE 1

A. Preparation of COSMOCIL and citrate complex.

12 g of diammonium citrate is dissolved in 88 g of deionized water. The solution is added dropwise to 225 g of COSMOCIL CQ (20%) containing 3 drops of Trition CF-10 dispersing aid. The concentration is about 13.8%. 138 g of sodium bicarbonate is dissolved in 1587 g of water and then added to the solution of the complex. This solution contains about 1.9% of active cosmocil-citric acid complex.

B. To the solution of part A is added 20 g of phenol with stirring and 7 g of citric acid.

The resulting composition can be sprayed onto clay for use as cat litter.

EXAMPLE 2

Step A. The following ingredients were mixed:

| Ingredients | Wt % |
| --- | --- |
| Water | 86.6 |
| Succinic acid | 2.5 |
| Phenol (90%) | 0.5 |
| Adogen | 0.4 |
| Ethanol | 10.0 |

A complex is formed between succinic acid and Adogen and the phenol and Adogen complex.

Step B. To the mixture of Step A were added the following:

| Ingredients | Wt % |
| --- | --- |
| O-phenylphenol | 0.5 |

The combination of Step A alone is suitable for use as an antimicrobial composition. However, the combination of Steps A and B provide a composition having a broad spectrum of antimicrobial activity, which lasts for at least 28 days.

The pH of the mixture was 6.5. The composition of step A and B were sprayed onto a commercial cat litter (PET STEP) so as to comprise about 2% by weight of litter. The resulting litter has acceptable to the cat and resulted in reduced odor after a one-week test.

EXAMPLE 3

A. An antimicrobial composition is prepared from the following ingredients:

| Ingredients | Wt % |
| --- | --- |
| Succinic Acid | 0.65 |
| Adogen 477 (50%) | 1.25 |
| Phenol | 0.65 |
| Ortho phenyl phenol | 0.65 |
| Water | 130.0 |

The Succinic acid is dissolved in 30 ml of water.

The phenol and orthophenyl phenol are added to 50 ml of water with stirring. The Cadogen is dissolved in 50 ml of water and added to the phenol solution. Then the succincic acid solution is added to phenol solution and stirred at 30*C. until a complete solution is formed.

B. Into a Banbury mixer is added 5 lbs of bentonite clay. The clay is constantly stirred while spraying the composition from part A until the clay contains about 2% by weight of the anti-microbial composition. The clay is continuously mixed until it is free of clumping.

The resulting composition can be used as cat litter.

What is claimed is:

1. A litter for use with pets which comprises absorbent clay particles containing an anti-microbial composition prepared by admixing:
   A. about 0.2 to 1.0 percent by weight of a diquaternary ammonium compound of the formula:

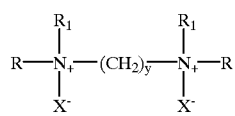

wherein:
   X is halogen or hydrogen;
   Y is an integer of 1 to 6;
   R is hydrogen or an alkyl of 1–7 carbon atoms; and
   $R_1$ is hydrogen or alkyl of 1–7 carbon atoms;
   B. about 0.2 to 1.0 percent by weight of a polycarboxylic acid of less than 10 carbon atoms;
   C. about 0.8 to 2.0 percent by weight of at least one phenol compound, and
   D. the remainder being an aqueous carrier
   said phenol and diquaternary compound forming complexes.

2. The litter of claim 1 wherein two phenols are utilized.

3. The litter of claim 2 wherein said phenols are phenol and orthophenyl phenol.

4. The litter of claim 1 wherein said diquaternary ammonium compound is a quaternary alkyl pentamethyl diammonium compound.

5. The litter of claim 4 wherein said compound is N-oleyl-1,3 propane diamine.

6. The litter of claim 1 wherein said polycarboxylic acid is selected from the group consisting of oxalic acid, maleic acid, succinic acid and citric acid.

7. The litter of claim 1 wherein said clay is selected from the group consisting of bentonite, attapulgite, and ground clay.

8. The litter of claim 1 including an odor absorbing or a neutralizing compound selected from the group consisting of sodium perborate, sodium phosphate, sodium carbonate, sodium bicarbonate and mixtures thereof.

9. The litter of claim 1 comprising about 1 to 10% by weight of said anti-microbial composition.

10. In a pet litter comprising clay particles the improvement which comprises including in said litter an antimicrobial composition formed by admixing at least about 0.2 percent of succinic acid, at least about 0.2 percent of N-oleyl-1, 3-propane diamine, at least about 0.2 percent of phenol and at least about 0.2 percent of ortho phenylphenol in water, said antimicrobial composition consisting about 1 to 5% by weight of said clay particles.

* * * * *